United States Patent [19]

Mita et al.

[11] Patent Number: 5,292,767

[45] Date of Patent: Mar. 8, 1994

[54] TETRAHYDROTHIOPHENE DERIVATIVES

[75] Inventors: Shiro Mita, Ashiya; Yoichi Kawashima, Kyoto; Nobuharu Kato, Osaka; Hiroshi Suhara, Osaka; Koji Yoneda, Osaka; Masataka Morishita, Osaka, all of Japan

[73] Assignee: Santen Pharmaceutical Co., Ltd., Osaka, Japan

[21] Appl. No.: 19,202

[22] Filed: Feb. 18, 1993

[30] Foreign Application Priority Data

Feb. 28, 1992 [JP] Japan .................. 4-79249

[51] Int. Cl.$^5$ .................. A01N 43/08; A61K 31/38; C07D 409/12; C07D 233/54
[52] U.S. Cl. .................. 514/444; 514/448; 549/59; 549/60; 549/71; 548/315.1
[58] Field of Search .............. 549/71, 60, 59; 514/448, 444; 548/315.1

[56] References Cited

FOREIGN PATENT DOCUMENTS 92-12129 7/1992 World Int. Prop. O. .

OTHER PUBLICATIONS

Chemical Abstracts, vol. 109, No. 17, Oct. 24, 1988, Columbus, OH. US; Abstract No. 149494r, Inoue, Yoshihiko and Al 'A wittig type arrangement of 2-methoxycarbonyl-2-phenyl-1,3-dithane and 2,2-diphenyl-1,3-dithiepane', p. 733; column R; of Bull. Inst. Chem. Res. Kyoto Univ., vol. 65, No. 3, 1987, pp. 121-124.

Bach et al., Thymulin, A Zinc-Dependent Hormone, Med. Oncol. & Tumor Pharmacother, vol. 6, No. 1, pp. 25-29, 1989, Great Britain.

Primary Examiner—Allen J. Robinson
Assistant Examiner—Deborah Lambkin
Attorney, Agent, or Firm—Frishauf, Holtz, Goodman & Woodward

[57] ABSTRACT

A compound of the formula [I] and pharmaceutically acceptable salts thereof; and a synthetic intermediate represented by the formula [II] and pharmaceutically acceptable salts thereof,

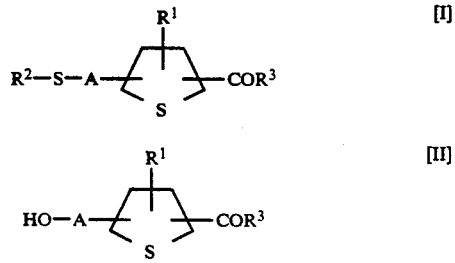

wherein
  R 1 is hydrogen or lower alkyl;
  R 2 is hydrogen or a protective group of thiol;
  R 3 is hydroxy, a remainder of ester group or a remainder of amido group;
  A is straight or branched lower alkylene, and
  the sulfur atom in the side chain may be directly join with —CO— to conform a thiolactone ring.

The compounds of this invention have excellent thymulin-like activities and are expected to be useful for treatment of various immune disorders such as immunodeficiency and autoimmune diseases.

15 Claims, No Drawings

TETRAHYDROTHIOPHENE DERIVATIVES

FIELD OF THE INVENTION

This invention relates to the novel tetrahydrothiophene derivatives which are useful for treatment of various immune disorders such as immunodeficiency and autoimmune diseases, and synthetic intermediates thereof.

BACKGROUND OF THE INVENTION

There are many active studies on mechanisms and therapeutic agents for various immune disorders or immune depression caused by carcinostatic drugs. It is known that thymulin, a nonapeptide produced in the thymus, forms a complex with zinc and improves a depressed immunity (Med. Oncol. & Tumor Pharmacother. 6, 25-29, 1989).

However, there remain many problems in practical use of thymulin. For example, the availability of thymulin is limited due to a small yield in the thymus and duration of the activity thereof is short because thymulin is easily decomposed by endogenous enzymes.

Therefore, synthetic compounds are desired which have a long lasting activity and can be prepared in a large amount. As such synthetic compounds, lactone or lactam compounds having two intramolecular sulfur atoms in the side chains are proposed (PCT/JP92/00002). As shown in the PCT application, the lactone or lactam compounds show excellent thymulin-like activities.

However, it is further desired to study other useful compounds such as different heterocycles.

The inventors focused on lactone derivatives having two sulfur atoms in their side chains, which were disclosed in PCT/JP92/00002, and studied to take one sulfur atom in a ring system, and succeeded in obtaining novel tetrahydrothiophene derivatives which have excellent thymulin-like activities.

DETAILED DESCRIPTION OF THE INVENTION

This invention relates to a compound of the formula [I] and pharmaceutically acceptable salts thereof; and a synthetic intermediate represented by the formula [II] and pharmaceutically acceptable salts thereof,

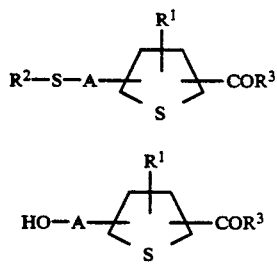

wherein
$R^1$ is hydrogen or lower alkyl;
$R^2$ is hydrogen or a protective group of thiol;
$R^3$ is hydroxy, a remainder of ester group or a remainder of amido group;
A is straight or branched lower alkylene, and the sulfur atom in the side chain may be directly joined with —CO— to conform a thiolactone ring.
The same shall be applied hereinafter.

The term "a protective group of thiol" intends to designate conventional protective groups exemplified by lower alkyl, lower alkenyl, lower alkanoyl, phenyl lower alkyl, phenylcarbonyl, phenyl lower alkylcarbonyl, trityl and tetrahydropyranyl, and the phenyl ring of the said phenyl lower alkyl, phenylcarbonyl or phenyl lower alkylcarbonyl can be substituted by lower alkyl, lower alkoxy, halogen, carboxy, lower alkoxycarbonyl, etc.

The term "a remainder of ester group" intends to designate groups, which can be converted into carboxylic acid by hydrolysis etc., exemplified by lower alkoxy, lower alkenyloxy, phenyl lower alkoxy and N-succinimidoxy, and the phenyl ring of the said phenyl lower alkoxy can be substituted by lower alkyl, lower alkoxy, halogen, carboxy, lower alkoxycarbonyl, etc.

The term "a remainder of amido group" intends to designate groups exemplified by amino and lower alkylamino, and the lower alkyl of the said lower alkylamino can be substituted by imidazolyl, carboxy, amino, lower alkylamino, lower alkoxycarbonylamino, phenyl lower alkoxycarbonylamino, hydroxy, etc., and the phenyl ring of the said phenyl lower alkoxycarbonylamino can be substituted by lower alkyl, lower alkoxy, halogen, carboxy, lower alkoxycarbonyl, etc.

The terms defined above are explained as follows in more detail.

The term "lower alkyl" intends to designate straight or branched alkyl having 1 to 6 carbon atoms exemplified by methyl, ethyl, propyl, hexyl, iso-propyl and t-butyl. The term "lower alkenyl" intends to designate straight or branched alkenyl having 2 to 6 carbon atoms containing double bond exemplified by vinyl, allyl and hexenyl. The term "lower alkanoyl" intends to designate straight or branched alkanoyl having 2 to 6 carbon atoms exemplified by acetyl, propionyl, hexanoyl, iso-propionyl and pivaloyl. The term "lower alkoxy" intends to designate straight or branched alkoxy having 1 to 6 carbon atoms exemplified by methoxy, ethoxy, propoxy, hexyloxy, iso-propoxy and tert-butoxy. The term "halogen" intends to designate fluorine, chlorine, bromine and iodine. The term "lower alkylene" intends to designate straight or branched alkylene having 1 to 6 carbon atoms exemplified by methylene, ethylene, trimethylene, tetramethylene, hexamethylene, (dimethyl)-methylene and (diethyl)methylene.

Examples of the pharmaceutically acceptable salts are a sodium salt, potassium salt, calcium salt, magnesium salt, zinc salt, hydrochloric acid salt and sulfuric acid salt.

Typical synthetic methods of the compounds of the formula [I] are shown in the following a) and b).

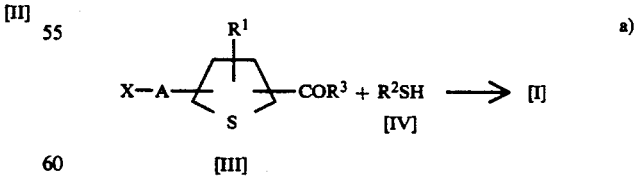

Wherein, X is a reactive group such as hydroxy, halogen, alkanoyloxy, alkylsulfonyl or arylalkylsulfonyl.

As shown in the above reaction scheme, the method a) is a reaction of a compound of the formula [III] with a thiol compound of the formula [IV] or salts thereof. The compound of the formula [III] can be prepared by the usual method. For example, a ester compound of the formula [V] is converted into a hydroxy compound of the formula [II] by a reduction as shown in the following scheme. If necessary, the compound [II] can be further converted into a halogen compound, etc. by the usual method.

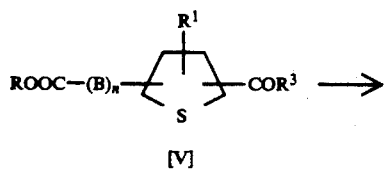

[V]

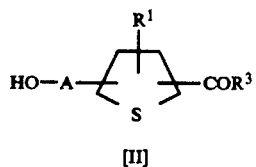

[II]

Wherein, n is 0 or 1, B is straight or branched lower alkylene.

The compounds of the formula [II] are novel compounds which are very useful intermediates for a synthesis of the compounds of this invention represented by the formula [I].

The compound of the formula [III] can be also prepared by following cyclization reaction.

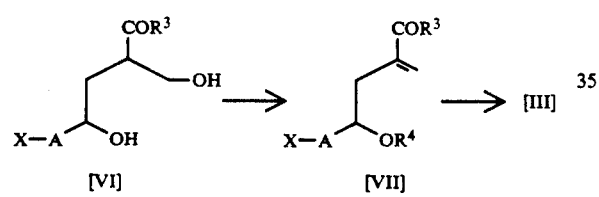

Wherein, $R^4$ is a reactive group such as methanesulfonyl.

The above method is that the diol compound of the formula [VI] is derived to the compound of the formula [VII] by dehydration followed by cyclization using sodium hydrogen sulfide, etc.

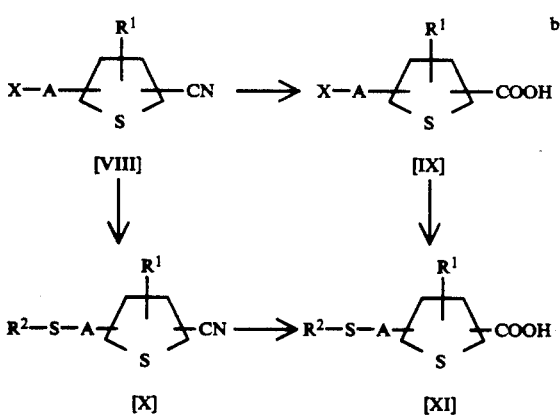

As shown in the above reaction scheme, the method b) is a hydrolysis reaction of a nitrile compound.

In the methods a) and b), when $R^2$ is a protective group of thiol, such protective group can be introduced or removed by the usual method in a desirable reaction step.

When $R^3$ is a remainder of ester or amido group, such group can be introduced in a desirable reaction step and, if necessary, can be removed in a desirable reaction step.

The compound wherein $R^3$ is a remainder of amido group can be prepared by the method a) using an amido compound as a starting substance or by a conventional method for an amido-bond formation.

Further, the amido compound can be easily prepared from a carboxylic acid derivative via a compound of the formula [XII].

The reaction schema is shown in the following c) method.

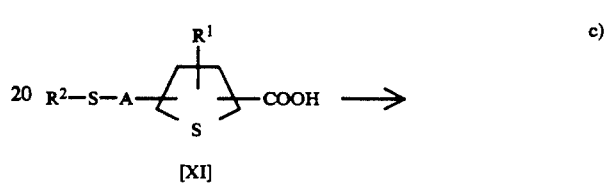

[XI]

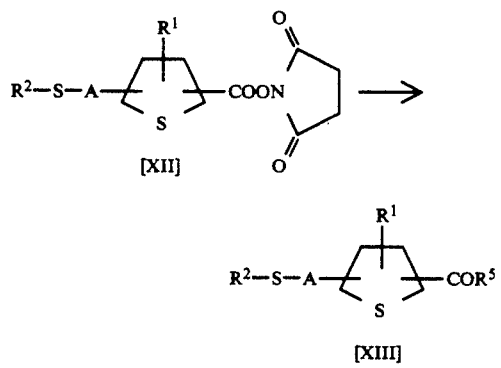

[XII]

[XIII]

Wherein, $R^5$ is a remainder of amido group.

In addition, as shown in following d) method, the compounds of this invention can be prepared by hydrolysis of the lactone compound, which was disclosed in PCT/JP92/00002, of the formula [XIV] having two sulfur atoms in the side chains.

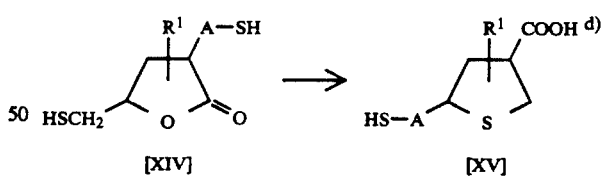

[XIV]      [XV]

The compounds prepared by the above methods can be converted into the salts as mentioned before by the usual method.

The compounds of the formula [I] and [II] have optical isomers or stereoisomers, and these isomers are included in this invention.

An optical active compound can be prepared by using an optical active starting substance. When a racemic compound is used as a starting substance, an optical resolution method using an optical resolving agent or column chromatograph can be followed to produce an optical active compound.

Stereoisomers can be separated by various methods. One of the separation method is based on the structural difference of the cis-form and the trans-form. Namely, the cis-compound can be derived to thiolactone of the compound of the formula [XVI] and separated from the mixture.

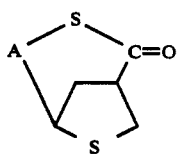
[XVI]

In the specification, the indication of cis and trans means that the conformation of —COR³ and —A—S—R² is cis or trans. When a compound is a mixture of cis- and trans-form or the conformation of cis or trans is not identified, such indication is not given.

The compounds of this invention are novel tetrahydrothiophene derivatives and the structural characteristic thereof is that one sulfur atom exist in one side chain and one carboxy group exist in other side chain. The basic structure is represented by the formula [XVII], and of course SH group can be protected by a conventional protective group of thiol and —COOH group can be converted into ester or amido.

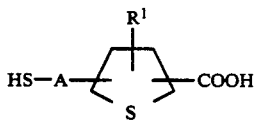
[XVII]

The compounds of this invention have excellent thymulin-like activities as shown in the article of pharmacological test and are expected to be useful for treatment of various immune disorders such as immunodeficiency and autoimmune diseases. There are various immune disorders, for example, rheumatoid arthritis, chronic hepatitis, anemia, systemic lupus erythematosus, primary immunodeficiency, or agammaglobulinemia. The compounds of this invention are expected to be useful for treatment of such diseases.

The therapeutic effect can be attained by an administration of the compound of this invention, but more effectively in a presence of zinc in conjunction with thymulin. Zinc can be supplied by an administration of a zinc salt such as zinc chloride together with the compound of this invention. But, without an external administration of zinc, the supply of zinc can be attained by an application of zinc which exists in a living body in a small amount.

The compounds of this invention can be administered orally or parenterally. As the dosage forms, tablet, capsule, soft capsule, injection, etc., can be used. The preparations can be produced by a usual method. For example, oral preparations such as a tablet, capsule, soft capsule and granule can be produced by adding a diluent such as lactose, starch, crystalline cellulose or vegetable oil; a lubricant such as magnesium stearate or talc; a binder such as hydroxypropyl cellulose or polyvinylpyrrolidone; a disintegrator such as carboxymethylcellulose calcium; a coating agent such as hydroxypropylmethylcellulose, macrogol or silicone resin; a coating film such as gelatin, if necessary. The dosage of the compounds of this invention can be adjusted depending on symptom, dosage form, etc. The usual daily dosage is 1-1000 mg, preferably 1-200 mg, which can be given in one or a few divided doses.

EXAMPLE

Reference Example 1 trans-4-tert-butoxycarbonyl-2-ethoxycarbonyltetrahydrothiophene (reference compound No.1) and cis-4-tert-butoxycarbonyl-2-ethoxycarbonyltetrahydrothiophene (reference compound No.2)

1) To a stirred solution of ethyl α-mercaptoacetate (1.6 g) in ethanol (15 ml), potassium tert-butoxide (1.5 g) was added at $-10°-0°$ C. under nitrogen atmosphere, and the mixture was stirred for 10 minutes at room temperature. Under ice-cooling, tert-butyl 2-bromomethylacrylate (2.9 g) dissolved in ethanol (5 ml) was added to the reaction mixture and the mixture was stirred for 1 hour at room temperature. The reaction mixture was concentrated in vacuo and the residue was dissolved in ethyl acetate. The solution was washed with water and saturated sodium chloride solution, dried over anhydrous sodium sulfate and concentrated in vacuo. The oily residue was purified by a silica gel column chromatography to give 2.1 g (60%) of tert-butyl 2-(ethoxycarbonylmethylthiomethyl)acrylate.

IR(film, $cm^{-1}$): 2979, 1718, 1368, 1274, 1157.

2) To a stirred solution of tert-butyl 2-(ethoxycarbonylmethylthiomethyl)acrylate (1.0 g) in THF (8 ml), 60% sodium hydride suspended in oil (16 mg) was added under nitrogen atmosphere and the mixture was refluxed for 3 hours. To the reaction mixture, saturated aqueous ammonium chloride solution (10 ml) was added under ice-cooling. The mixture was stirred for 5 minutes and extracted with ethyl acetate. The organic layer was washed with saturated sodium chloride solution, dried over anhydrous sodium sulfate and concentrated in vacuo. The oily residue was purified by a silica gel column chromatography to give 0.3 g (30%) of the reference compound No.1 and 0.22 g (21%) of the reference compound No.2.

reference compound No. 1:
IR(film, $cm^{-1}$): 2979, 1729, 1368, 1155.
reference compound No. 2:
IR(film, $cm^{-1}$): 2978, 1734, 1368, 1271, 1152.

Following compound can be prepared by the similar method as Reference Example 1.

trans-4-tert-butoxycarbonyl-2-ethoxycarbonyl-2-methyltetrahydrothiophene (reference compound No. 3)

IR(film, $cm^{-1}$): 2978, 2934, 1727, 1458, 1368, 1274, 1155.

Reference Example 2 trans-4-tert-butoxycarbonyl-3-ethoxycarbonyltetrahydrothiophene (reference compound No.4)

To a stirred solution of fumaric acid tert-butyl ethyl diester (1.4 g) and chloromethyl-(trimethylsilyl)methylsulfide (1.0 g) in acetonitrile (24 ml), cesium fluoride (1.9 g) was added and the mixture was stirred for 4 days at room temperature. To the reaction mixture, diethylether and water were added. The organic layer was washed with saturated sodium chloride solution, dried over anhydrous magnesium sulfate and concentrated in vacuo. The oily residue was purified by a silica gel column chromatography to give 0.98 g (64%) of the reference compound No.4.

IR(film, $cm^{-1}$): 2979, 1731, 1368, 1259, 1156.

Reference Example 3 trans-5-tert-butoxycarbonyl-2-ethoxycarbonyltetrahydrothiophene (reference compound No.5) and cis-5-tert-butoxycarbonyl-2-ethoxycarbonyltetrahydrothiophene (reference compound No.6)

1) To a stirred solution of diethyl 2,5-dibromoadipate (4.5 g) in dimethylformamide (15 ml), sodium sulfide enneahydrate (3.9 g) was added under nitrogen atmosphere and the mixture was stirred for 5 hours under ice-cooling. To the reaction mixture, diethyl ether and water were added. The organic layer was washed with saturated sodium chloride solution, dried over anhydrous magnesium sulfate and concentrated in vacuo. The oily residue was purified by a silica gel column chromatography to give 2.1 g (72%) of 2,5-diethoxycarbonyltetrahydrothiophene.

IR(film, $cm^{-1}$): 2981, 1732, 1445, 1369, 1330, 1301, 1198, 1034.

2) To a solution of 2,5-diethoxycarbonyltetrahydrothiophene (2.4 g) in ethanol (10 ml), potassium hydroxide (0.64 g) dissolved in ethanol (10 ml) was added dropwise and the mixture was stirred for 1 hour at room temperature. To the reaction mixture, diethyl ether and water were added. Aqueous layer was acidified with 2N hydrochloric acid and extracted with ethyl acetate. The organic layer was washed with saturated sodium chloride solution, dried over anhydrous sodium sulfate and concentrated in vacuo to give 1.6 g (78%) of 2-carboxy-5-ethoxycarbonyltetrahydrothiophene.

IR(film, $cm^{-1}$): 2982, 1735, 1712, 1444, 1417, 1372, 1300, 1194, 1027.

3) Isobutene (10 ml), 2-carboxy-5-ethoxycarbonyltetrahydrothiophene (2.1 g) dissolved in diethyl ether (3 ml) and concentrated sulfuric acid (0.1 ml) were put into a sealed tube under nitrogen atmosphere and dry ice - methanol cooling. After sealing, the mixture was stirred over night at room temperature. The reaction mixture was added into aqueous sodium bicarbonate solution in a small portion and extracted with diethyl ether. The organic layer was washed with saturated sodium chloride solution, dried over anhydrous magnesium sulfate and concentrated in vacuo. The oily residue was purified by a silica gel column chromatography to give 0.79 g (29%) of the reference compound No.5 and 0.97 g (35%) of the reference compound No.6.

reference compound No.5:
IR(film, $cm^{-1}$): 2979, 1731, 1368, 1299, 1152.
reference compound No.6:
IR(film, $cm^{-1}$): 2979, 1737, 1369, 1296, 1149.

EXAMPLE 1 trans-4-tert-butoxycarbonyl-2-hydroxymethyltetrahydrothiophene (compound No. 1-1)

Lithium bromide (686 mg) and sodium borohydride (165 mg) were dissolved in ethanol (6 ml) and under nitrogen atmosphere the mixture was stirred for 1 hour at room temperature. To the mixture, trans-4-tert-butoxycarbonyl-2-ethoxycarbonyltetrahydrothiophene (ref. compound No. 1, 567 mg) dissolved in ethanol (2 ml) was added at room temperature and the mixture was stirred for 18 hours. Aqueous ammonium chloride solution and saturated sodium chloride solution were added to the mixture and extracted with ethyl acetate. The organic layer was washed with saturated sodium chloride solution, dried over anhydrous sodium sulfate and concentrated in vacuo. The oily residue was purified by a silica gel column chromatography to give 436 mg (99%) of the titled compound (compound No. 1-1).

IR(film, $cm^{-1}$): 3428, 2977, 2935, 1726, 1368, 1153.

Following compounds can be prepared by the similar method as Example 1.

cis-4-tert-butoxycarbonyl-2-hydroxymethyltetrahydrothiophene (compound No. 1-2)
IR(film, $cm^{-1}$): 3432, 2976, 2933, 1725, 1368, 1255, 1153.

trans-4-tert-butoxycarbonyl-2-hydroxymethyl-2-methyltetrahydrothiophene (compound No. 1-3)
IR(film, $cm^{-1}$): 3436, 2976, 2931, 2867, 1729, 1456, 1392, 1369, 1257, 1154.

trans-4-tert-butoxycarbonyl-3-hydroxymethyltetrahydrothiophene (compound No. 1-4)
IR(film, $cm^{-1}$): 3435, 2977, 2036, 1726, 1455, 1393, 1368, 1256, 1154, 1051, 848.

trans-5-tert-butoxycarbonyl-2-hydroxymethyltetrahydrothiophene (compound No. 1-5)
IR(film, $cm^{-1}$): 3435, 2977, 2935, 1729, 1454, 1393, 1369, 1150, 1070.

cis-5-tert-butoxycarbonyl-2-hydroxymethyltetrahydrothiophene (compound No. 1-6)
IR(film, $cm^{-1}$): 3435, 2977, 2934, 1728, 1455, 1393, 1369, 1350, 1298, 1250, 1151, 846.

EXAMPLE 2

4-tert-butoxycarbonyl-2-(2-hydroxyethyl)tetrahydrothiophene (compound No. 2-1)

1) To a stirred solution of tert-butyl 4-hydroxy-2-hydroxymethyl-6-tetrahydropyranyloxyhexanoate (0.28 g) and triethylamine (0.56 g) in methylene chloride (20 ml), mesylchloride (0.56 g) dissolved in methylene chloride (10 ml) was added dropwise under nitrogen atmosphere and ice-cooling. The mixture was stirred for 2 hours at room temperature and concentrated in vacuo. Saturated aqueous sodium bicarbonate solution was added to the oily residue and extracted with ethyl acetate. The organic layer was washed with saturated aqueous sodium bicarbonate solution, 1N hydrochloric acid, water and saturated aqueous sodium chloride solution. The organic layer was dried over anhydrous magnesium sulfate and concentrated in vacuo. The oily residue was dissolved in benzene (20 ml), and 1,8-diazabicyclo[5.4.0]undec-7-ene (0.2 g) was added to the solution. The mixture was stirred for 3 hours. Aqueous citric acid solution was added to the mixture and extracted with ethyl acetate. The organic layer was washed with saturated aqueous sodium bicarbonate solution, water and saturated sodium chloride solution. The organic layer was dried over anhydrous magnesium sulfate and concentrated in vacuo. The oily residue was purified by a silica gel column chromatography to give 0.22 g (31%) of tert-butyl 4-mesyloxy-2-methylene-6-tetrahydropyranyloxyhexanoate.

IR (film, $cm^{-1}$): 2938, 1713, 1632, 1335, 1174, 1048, 911.

2) To a stirred solution of tert-butyl 4-mesyloxy-2-methylene-6-tetrahydropyranyloxyhexanoate (1.38 g) in dimethylformamide (20 ml), sodium hydrosulfide hydrate (0.34 g) was added under nitrogen atmosphere and ice-cooling and the mixture was stirred for 7 hours. Water was added to the mixture and extracted with diethylether. The organic layer was washed with saturated aqueous sodium bicarbonate solution, water and saturated sodium chloride solution. The organic layer was dried over anhydrous magnesium sulfate and concentrated in vacuo. The oily residue was purified by a silica gel column chromatography to give 0.67 g (58%) of 4-tert-butoxycarbonyl-2-(2-tetrahydropyranyloxyethyl)tetrahydrothiophene.

IR (film, cm$^{-1}$): 2940, 2870, 1728, 1454, 1392, 1367, 1258, 1154, 1077, 1034, 938, 869, 848.

3) To a stirred solution of 4-tert-butoxycarbonyl-2-(2-tetrahydropyranyloxyethyl)tetrahydrothiophene (0.67 g) in methanol (20 ml), p-toluenesulfonic acid monohydrate (40 mg) was added and the mixture was stirred for 3 hours at room temperature. Saturated aqueous sodium bicarbonate solution was added to the mixture and extracted with ethyl acetate. The organic layer was washed with water and saturated sodium chloride solution, dried over anhydrous magnesium sulfate and concentrated in vacuo. The oily residue was purified by a silica gel column chromatography to give 470 mg (96%) of the titled compound (compound No. 2-1).

IR (film, cm$^{-1}$): 3430, 2933, 1729, 1455, 1393, 1368, 1058, 847.

EXAMPLE 3 trans-5-tert-butoxycarbonyl-2-(2-hydroxyethyl)tetrahydrothiophene (compound No. 3-1)

1) To a stirred solution of trans-5-tert-butoxycarbonyl-2-hydroxymethyltetrahydrothiophene (compound No. 1-5, 5.0 g) in anhydrous diethylether (80 ml), triphenylphosphine (9.7 g) and carbon tetrachloride (5.7 g) are added under nitrogen atmosphere and the mixture is stirred for 2 hours at room temperature. n-Hexane (200 ml) is added to the mixture and filtrated. The filtrate is concentrated in vacuo. The oily residue is purified by a silica gel column chromatography to give trans-5-tert-butoxycarbonyl-2-chloromethyltetrahydrothiophene.

2) To a stirred solution of trans-5-tert-butoxycarbonyl-2-chloromethyltetrahydrothiophene (3.5 g) in dimethylformamide (15 ml), sodium cyanide (1.5 g) is added and the mixture was stirred for 5 hours at 60°–70° C. 5% aqueous citric acid solution is added to the mixture and extracted with ethyl acetate - benzene (1:1). The organic layer is washed with water and saturated aqueous sodium chloride solution, dried over anhydrous sodium sulfate and concentrated in vacuo. The oily residue is purified by a silica gel column chromatography to give trans-5-tert-butoxycarbonyl-2-cyanomethyltetrahydrothiophene.

3) To a stirred solution of trans-5-tert-butoxycarbonyl-2-cyanomethyltetrahydrothiophene (2.3 g) in diethylether (100 ml), 1M diisobutyl-aluminiumhydride dissolved in hexane (12.1 ml) is added at −30° C. and the mixture is stirred for 2 hours at −20°--−10° C. 10% aqueous citric acid solution is added to the mixture and extracted with ethyl acetate - benzene (1:1). The organic layer is washed with 10% aqueous citric acid solution, water and saturated sodium chloride solution. The organic layer is dried over anhydrous sodium sulfate and concentrated in vacuo. The oily residue was purified by a silica gel column chromatography to give trans-5-tert-butoxycarbonyl-2-formylmethyltetrahydrothiophene.

4) To a stirred solution of trans-5-tert-butoxycarbonyl-2-formylmethyltetrahydrothiophene (1.2 g) in ethanol, sodium borohydride (0.3 g) is added under ice-cooling and the mixture is stirred for 1 hour. Saturated sodium chloride solution is added to the mixture under ice-cooling and extracted with ethyl acetate. The organic layer is dried over anhydrous sodium sulfate and concentrated in vacuo. The oily residue is purified by a silica gel column chromatography to give the titled compound (compound No. 3-1).

Following compounds can be prepared by the similar method as Example 3.

cis-5-tert-butoxycarbonyl-2-(2-hydroxyethyl)tetrahydrothiophene (compound No. 3-2)

trans-5-tert-butoxycarbonyl-2-(3-hydroxypropyl)tetrahydrothiophene (compound No. 3-3)

trans-4-tert-butoxycarbonyl-3-(2-hydroxyethyl)tetrahydrothiophene (compound No. 3-4)

EXAMPLE 4 trans-2-acetylthiomethyl-4-tert-butoxycarbonyltetrahydrothiophene (compound No. 4-1)

To a stirred solution of triphenylphosphine (391 mg) in THF (3 ml), azodicarboxylic acid diethylester (260 mg) dissolved in THF (1 ml) was added at −15°--−10° C. under nitrogen atmosphere. To the mixture, trans-4-tert-butoxycarbonyl-2-hydroxymethyltetrahydrothiophene (compound No. 1-1, 150 mg) and thioacetic acid (114 mg) dissolved in THF (2 ml) were added at −20°--−15° C., and the mixture was stirred for 1 hour at −20° C. and for 1 hour at room temperature. The mixture was concentrated in vacuo. The oily residue was purified by a silica gel column chromatography to give 169 mg (82%) of the titled compound (compound No. 4-1).

IR(film, cm$^{-1}$): 2976, 1726, 1696, 1367, 1153.

Following compounds can be prepared by the similar method as Example 4.

cis-2-acetylthiomethyl-4-tert-butoxycarbonyltetrahydrothiophene (compound No. 4-2)

IR(film, cm$^{-1}$): 2976, 1726, 1695, 1367, 1276, 1152.

trans-2-acetylthiomethyl-4-tert-butoxycarbonyl-2-methyltetrahydrothiophene (compound No. 4-3)

IR(film, cm$^{-1}$): 2976, 2928, 1727, 1696, 1455, 1368, 1256, 1154, 625.

trans-3-acetylthiomethyl-4-tert-butoxycarbonyltetrahydrothiophene (compound No. 4-4)

IR(film, cm$^{-1}$): 2977, 2932, 1726, 1694, 1477, 1455, 1392, 1368, 1255, 1151, 848, 626.

trans-2-acetylthiomethyl-5-tert-butoxycarbonyltetrahydrothiophene (compound No. 4-5)

mp 52.7°–53.5° C. (n-hexane - ethyl acetate).

IR(KBr, cm$^{-1}$): 2978, 2940, 1726, 1692, 1367, 1223, 1152, 624.

cis-2-acetylthiomethyl-5-tert-butoxycarbonyltetrahydrothiophene (compound No. 4-6)

IR(film, cm$^{-1}$): 2977, 2932, 1728, 1694, 1478, 1454, 1393, 1368, 1352, 1258, 1150, 957, 734, 627.

2-(2-acetylthioethyl)-4-tert-butoxycarbonyltetrahydrothiophene (compound No. 4-7)

IR (film, cm$^{-1}$): 2976, 2931, 1726, 1693, 1454, 1392, 1367, 1258, 1152, 954, 847, 755.

trans-2-(2-acetylthioethyl)-5-tert-butoxycarbonyltetrahydrothiophene (compound No. 4-8)

cis-2-(2-acetylthioethyl)-5-tert-butoxycarbonyltetrahydrothiophene (compound No. 4-9)

trans-2-(3-acetylthiopropyl)-5-tert-butoxycarbonyltetrahydrothiophene (compound No. 4-10)

trans-3-(2-acetylthioethyl)-4-tert-butoxycarbonyltetrahydrothiophene (compound No. 4-11)

trans-4-tert-butoxycarbonyl-2-propanoylthiomethyltetrahydrothiophene (compound No. 4-12)

trans-4-tert-butoxycarbonyl-2-benzoylthiomethyltetrahydrothiophene (compound No. 4-13)

trans-4-tert-butoxycarbonyl-2-(4-methylbenzoyl)thiomethyltetrahydrothiophene (compound No. 4-14)

trans-4-tert-butoxycarbonyl-2-(4-methoxybenzoyl)thiomethyltetrahydrothiophene (compound No. 4-15)

trans-4-tert-butoxycarbonyl-2-(4-chlorobenzoyl)thiomethyltetrahydrothiophene (compound No. 4-16)

trans-4-tert-butoxycarbonyl-2-benzylthiomethyltetrahydrothiophene (compound No. 4-17)

trans-4-tert-butoxycarbonyl-2-(4-methylbenzyl)thiomethyltetrahydrothiophene (compound No. 4-18)

trans-4-tert-butoxycarbonyl-2-(4-methoxybenzyl)thiomethyltetrahydrothiophene (compound No. 4-19)

trans-4-tert-butoxycarbonyl-2-(4-chlorobenzyl)thiomethyltetrahydrothiophene (compound No. 4-20)

trans-4-tert-butoxycarbonyl-2-phenylacetylthiomethyltetrahydrothiophene (compound No. 4-21)

EXAMPLE 5

(2R)-2-acetylthiomethyl-4-tert-butoxycarbonyltetrahydrothiophene (compound No. 5-1)

1) To a stirred solution of tert-butyl (4S)-5-chloro-4-hydroxy-2-hydroxymethylpentanoate (10.0 g) and triethylamine (12.7 g) in methylene chloride (100 ml), mesyl chloride (11.5 g) was added dropwise under ice-cooling and the mixture was stirred for 20 minutes. The mixture was concentrated in vacuo. Water was added to the residue and extracted with ethyl acetate. The organic layer was washed with saturated aqueous sodium bicarbonate solution, water and saturated aqueous sodium chloride solution. The organic layer was dried over anhydrous magnesium sulfate and concentrated in vacuo. The oily residue was dissolved in benzene (130 ml) and 1,8-diazabicyclo[5.4.0]undec-7-ene (7.0 g) was added to the solution. The mixture was stirred for 2 hours at room temperature. Water was added to the mixture and extracted with ethyl acetate. The organic layer was washed with water and saturated sodium chloride solution, dried over anhydrous magnesium sulfate and concentrated in vacuo. The oily residue was purified by a silica gel column chromatography to give 11.1 g (89%) of tert-butyl (4S)-5-chloro-4-mesyloxy-2-methylenepentanoate.

$[\alpha]_D^{20}$ −1.6. (c=1.0, chloroform).

IR (film, cm$^{-1}$): 2978, 2938, 1707, 1633, 1367, 1255, 1175, 960, 916, 849, 798.

2) To a stirred solution of tert-butyl (4S)-5-chloro-4-mesyloxy-2-methylenepentanoate (5.0 g) in dimethylformamide (80 ml), sodium hydrosulfide hydrate (4.0 g) was added under ice-cooling and the mixture was stirred for 3.5 hours. Water was added to the mixture and extracted with diethylether. The organic layer was washed with water and saturated sodium chloride solution, dried over anhydrous magnesium sulfate and concentrated in vacuo. Potassium thioacetate (2.9 g) was added to the oily residue dissolved in ethanol (60 ml) and the mixture was refluxed for 10 minutes. Water was added to the mixture and extracted with diethylether. The organic layer was washed with water and saturated sodium chloride solution, dried over anhydrous magnesium sulfate and concentrated in vacuo. The oily residue was purified by a silica gel column chromatography to give 1.5 g (32%) of the titled compound (compound No. 5-1).

IR (film, cm$^{-1}$): 2976, 2932, 1726, 1694, 1456, 1392, 1368, 1278, 1153, 957, 847.

Following compounds can be prepared by the similar method as Example 5.

(2R)-2-benzoylthiomethyl-4-tert-butoxycarbonyltetrahydrothiophene (compound No. 5-2)

IR (film, cm$^{-1}$): 2977, 2932, 1726, 1665, 1581, 1448, 1368, 1207, 1152, 912, 846, 774, 689, 648.

2-acetylthiomethyl-4-tert-butoxycarbonyltetrahydrothiophene (compound No. 5-3)

IR (film, cm$^{-1}$): 2977, 2932, 1726, 1693, 1455, 1392, 1367, 1278, 1255, 1152, 957, 847, 626.

(2S)-2-acetylthiomethyl-4-tert-butoxycarbonyltetrahydrothiophene (compound No. 5-4)

IR (film, cm$^{-1}$): 2953, 2878, 1731, 1666, 1449, 1207, 1025, 1000, 912, 689.

2-acetylthiomethyl-4-isopropoxycarbonyltetrahydrothiophene (compound No. 5-5)

IR (film, cm$^{-1}$): 2979, 2935, 1727, 1692, 1454, 1373, 1271, 1179, 1134, 1107, 956, 909.

(2R)-2-acetylthiomethyl-4-isopropoxycarbonyltetrahydrothiophene (compound No. 5-6)

IR (film, cm$^{-1}$): 2979, 2935, 1729, 1693, 1454, 1373, 1272, 1179, 1107, 956, 909, 824, 700.

2-acetylthiomethyl-4-ethoxycarbonyltetrahydrothiophene (compound No. 5-7)

IR (film, cm$^{-1}$): 2980, 2934, 1731, 1693, 1444, 1371, 1353, 1179, 1134, 1032, 957, 862.

2-acetylthiomethyl-4-methoxycarbonyltetrahydrothiophene (compound No. 5-8)

IR (film, cm$^{-1}$): 2950, 1735, 1690, 1435, 1356, 1272, 1170, 1134, 957, 626.

EXAMPLE 6 trans-2-acetylthiomethyl-4-carboxytetrahydrothiophene (compound No. 6-1)

To a stirred solution of trans-2-acetylthiomethyl-4-tert-butoxycarbonyltetrahydrothiophene (compound No. 4-1, 130 mg) in methylene chloride (2 ml), trifluoroacetic acid (1 ml) was added and the mixture was stirred for 2 hours at room temperature. The mixture was concentrated in vacuo and the oily residue was purified by a silica gel column chromatography to give 112 mg (quantitative yield) of the titled compound (compound No. 6-1) as white powder.

IR (KBr, cm$^{-1}$): 2926, 1691, 1431, 1295, 1134.

Following compounds can be prepared by the similar method as Example 6.

cis-2-acetylthiomethyl-4-carboxytetrahydrothiophene (compound No. 6-2)

IR (KBr, cm$^{-1}$): 2917, 1695, 1291, 1134, 958.

trans-2-acetylthiomethyl-4-carboxy-2-methyltetrahydrothiophene (compound No. 6-3)

mp 90.5°–94.5° C.

IR (KBr, cm$^{-1}$): 2927, 1691, 1423, 1291, 1239, 1224, 1130, 960, 624.

trans-3-acetylthiomethyl-4-carboxytetrahydrothiophene (compound No. 6-4)

mp 73.9°–75.8° C. (n-hexane - ethyl acetate).

IR (KBr, cm$^{-1}$): 2937, 1692, 1421, 1292, 1260, 1141, 945, 633.

trans-2-acetylthiomethyl-5-carboxytetrahydrothiophene (compound No. 6-5)

mp 58.8°–60.0° C. (n-hexane - ethyl acetate).

IR (KBr, cm$^{-1}$): 2950, 1693, 1417, 1309, 1243, 1133, 625.

cis-2-acetylthiomethyl-5-carboxytetrahydrothiophene (compound No. 6-6)

mp 61.8°–62.8° C. (n-hexane - ethyl acetate).

IR (KBr, cm$^{-1}$): 2950, 1689, 1451, 1417, 1298, 1239, 1136, 961, 629.

(2R)-2-acetylthiomethyl-4-carboxytetrahydrothiophene (compound No. 6-7)

IR (KBr, cm$^{-1}$): 1690, 1421, 1353, 1287, 1245, 1136, 1105, 956, 756, 688, 627.

(2R)-2-benzoylthiomethyl-4-carboxytetrahydrothiophene (compound No. 6-8)

IR (KBr, cm$^{-1}$): 1699, 1660, 1580, 1417, 1278, 1210, 1175, 921, 774, 689, 647.

(2S)-2-acetylthiomethyl-4-carboxytetrahydrothiophene (compound No. 6-9)

IR (KBr, cm$^{-1}$): 2928, 1690, 1425, 1354, 1288, 1137, 959, 630.

2-(2-acetylthioethyl)-4-carboxytetrahydrothiophene (compound No. 6-10)

IR (film, cm$^{-1}$): 2929, 1692, 1422, 1355, 1268, 1132, 949.

EXAMPLE 7 trans-4-carboxy-2-mercaptomethyltetrahydrothiophene (compound No. 7-1)

Trans-2-acetylthiomethyl-4-carboxytetrahydrothiophene (compound No. 6-1, 50 mg) was dissolved in 1N ammonia water (2 ml) and the mixture was stirred for 30 minutes at room temperature. Under ice-cooling, the reaction mixture was acidified with 1N hydrochloric acid. Saturated sodium chloride solution added to the mixture and extracted with ethyl acetate. The organic layer was washed with saturated sodium chloride solution, dried over anhydrous sodium sulfate and concentrated in vacuo. The oily residue was purified by a silica gel column chromatography to give 35 mg (85%) of the titled compound (compound No. 7-1).

mp 57.3°–58.7° C. (n-hexane - ethyl acetate).

IR (KBr, cm$^{-1}$): 2523, 1698, 1450, 1414, 1331, 1299, 1269, 1234, 1201, 910, 788, 688.

Following compounds can be prepared by the similar method as Example 7.

cis-4-carboxy-2-mercaptomethyltetrahydrothiophene (compound No. 7-2)

mp 67.8°–69.0° C. (n-hexane - ethyl acetate)

IR (KBr, cm$^{-1}$): 2597, 1698, 1423, 1340, 1275, 1248, 1196, 942, 689.

trans-4-carboxy-2-mercaptomethyl-2-methyltetrahydrothiophene (compound No. 7-3)

mp 73.3°–74.2° C.

IR (KBr, cm$^{-1}$): 2930, 1699, 1422, 1264, 1210, 1110, 650.

trans-4-carboxy-3-mercaptomethyltetrahydrothiophene (compound No. 7-4)

mp 41.5°–46.2° C. (n-hexane - ethyl acetate)

IR (KBr, cm$^{-1}$): 2922, 1712, 1426, 1294, 1257, 1214, 1190, 935, 681.

trans-5-carboxy-2-mercaptomethyltetrahydrothiophene (compound No. 7-5)

mp 55.0°–57.5° C. (n-hexane - ethyl acetate).

IR (KBr, cm$^{-1}$): 2942, 2533, 1690, 1449, 1310, 1229, 902, 680.

cis-5-carboxy-2-mercaptomethyltetrahydrothiophene (compound No. 7-6)

IR (film, cm$^{-1}$): 2932, 2557, 1714, 1442, 1417, 1300, 1240, 686.

(2R)-4-carboxy-2-mercaptomethyltetrahydrothiophene (compound No. 7-7)

(2S)-4-carboxy-2-mercaptomethyltetrahydrothiophene (compound No. 7-8)

4-carboxy-2-(2-mercaptoethyl)tetrahydrothiophene (compound No. 7-9)

IR (film, cm$^{-1}$): 2929, 1698, 1424, 1275, 934.

(2R)-4-tert-butoxycarbonyl-2-mercaptomethyltetrahydrothiophene (compound No. 7-10)

IR (film, cm$^{-1}$): 2975, 2931, 2555, 1723, 1476, 1455, 1391, 1367, 1277, 1152, 846.

(2R,4R)-4-benzyloxycarbonyl-2-mercaptomethyltetrahydrothiophene (compound No. 7-11)

IR (film, cm$^{-1}$): 2936, 1732, 1497, 1454, 1166, 737, 698.

EXAMPLE 8 trans-4-carboxy-2-(1-mercapto-1-methylethyl)tetrahydrothiophene (compound No. 8-1)

To a stirred solution of cis-4-(1-mercapto-1-methylethyl)-2-mercaptomethyl-4-butanolide (1.1 g) in THF (4 ml), 1N sodium hydroxide solution (5.2 ml) was added and the mixture was stirred for 30 minutes. The reaction mixture was acidified with 1N hydrochloric acid and extracted with ethyl acetate. The organic layer was washed with saturated sodium chloride solution, dried over anhydrous sodium sulfate and concentrated in vacuo to give the titled compound (compound No. 8-1) quantitatively.

mp 97.0°–98.3° C. (n-hexane).

IR (KBr, cm$^{-1}$): 2948, 2888, 2635, 1697, 1451, 1261, 942.

Following compound can be prepared by the similar method as Example 8.

cis-4-carboxy-2-(1-mercapto-1-methylethyl)tetrahydrothiophene (compound No. 8-2)

IR (KBr, cm$^{-1}$): 3029, 2971, 2551, 1708, 1455, 1417, 1365, 1276, 918, 674.

EXAMPLE 9

(1R,5R)-3,6-dithia-2-oxobicyclo[3.2.1]octane (compound No. 9-1) and N-succinimidyl (2R,4R)-2-mercaptomethyltetrahydrothiophene-4-carboxylate (compound No. 9-2)

To a stirred solution of (2R)-4-carboxy-2-mercaptomethyltetrahydrothiophene (compound No. 7-7, 14.9 g) in methylene chloride (1600 ml), N-hydroxysuccinimide (10.6 g) and N,N'-dicyclohexylcarbodiimide (19.0 g) were added under nitrogen atmosphere and the mixture was stirred over night at room temperature. After removing the insoluble matter by filtration, the filtrate was concentrated in vacuo. The oily residue was purified by a silica gel column chromatography to give 5.3 g (40%) of the titled compound (compound No. 9-1) and 10.0 g (43%) of the titled compound (compound No. 9-2).

compound No. 9-1:

IR (KBr, cm$^{-1}$): 2944, 1662, 1432, 1309, 1268, 1218, 1134, 1041, 982, 901, 886, 826, 723.

compound No. 9-2:

IR (KBr, cm$^{-1}$): 2941, 2570, 1809, 1781, 1736, 1440, 1428, 1372, 1294, 1207, 1093, 1060, 992, 942.

Following compounds can be prepared by the similar method as Example 9.

(1S,5S)-3,6-dithia-2-oxobicyclo[3.2.1]octane (compound No. 9-3)

mp 57.0°–58.9° C. (benzene - n-hexane).

[α]$_D^{20}$ −181.8. (c=0.5, chloroform).

IR (KBr, cm$^{-1}$): 2944, 2910, 1662, 1432, 1309, 1268, 1218, 1134, 1060, 1041, 982, 826.

N-succinimidyl (2S,4S)-2-mercaptomethyltetrahydrothiophene-4-carboxylate (compound No. 9-4).

EXAMPLE 10

(2R,4R)-4-carboxy-2-mercaptomethyltetrahydrothiophene (compound No. 10-1)

To a stirred solution of N-succinimidyl (2R,4R)-2-mercaptomethyltetrahydrothiophene-4-carboxylate (compound No. 9-2, 10.0 g) in methanol (200 ml), 2N sodium hydroxide solution (200 ml) was added under ice-cooling and the mixture was stirred for 15 minutes. The mixture was washed with diethylether. Aqueous layer was acidified with 2N hydrochloric acid and extracted with diethylether. The organic layer was washed with water and saturated sodium chloride solution, dried over anhydrous sodium sulfate and concentrated in vacuo. The oily residue was purified by a silica gel column chromatography to give 5.8 g (90%) of the titled compound (compound No. 10-1). compound No. 10-1 mp 54.3°-55.9° C. (n-hexane - ethyl acetate).
$[\alpha]_D^{20}$ −131 2° (c=0.5, chloroform).
IR (KBr, cm$^{-1}$): 2917, 2670, 2558, 1689, 1416, 1287, 1245, 1217, 942, 687.

Following compound can be prepared by the similar method as Example 10.

(2S,4S)-4-carboxy-2-mercaptomethyltetrahydrothiophene (compound No. 10-2)

mp 54.5°-56.0° C. (n-hexane - ethyl acetate - diethylether).
IR (KBr, cm$^{-1}$): 3020, 2916, 2556, 1690, 1457, 1417, 1287, 1217, 1167, 944.

EXAMPLE 11

(2R,4S)-4-carboxy-2-mercaptomethyltetrahydrothiophene (compound No. 11-1)

To a stirred solution of (1R,5R)-3,6-dithia-2-oxobicyclo[3.2.1]octane (compound No.9-1, 0.22 g) in THF (10 ml), 1N sodium hydroxide solution (5 ml) was added at room temperature and the mixture was stirred for 30 minutes. The reaction mixture was washed with diethylether and the aqueous layer was acidified with 2N hydrochloric acid and extracted with ethyl acetate. The organic layer was washed with water and saturated sodium chloride solution, dried over anhydrous sodium sulfate and concentrated in vacuo. The oily residue was purified by a silica gel column chromatography to give 0.22 g (90%) of the titled compound (compound No. 11-1).

mp 64.5°-65.7° C. (n-hexane - ethyl acetate).
$[\alpha]_D^{20}$ −16.9° (c=0.5, chloroform).
IR (KBr, cm$^{-1}$): 2543, 1688, 1432, 1416, 1284, 1219, 1192, 945, 684, 674.

Following compound can be prepared by the similar method as Example 11.

(2S,4R)-4-carboxy-2-mercaptomethyltetrahydrothiophene (compound No. 11-2)

mp 62.0°-63.8° C. (n-hexane - ethyl acetate).
$[\alpha]_D^{20}$ +11.8° (c=0.5, chloroform).
IR (KBr, cm$^{-1}$): 2929, 2544, 1687, 1416, 1283, 1220, 1192, 944.

EXAMPLE 12 trans-4-ethoxycarbonyl-2-(1-mercapto-1-methylethyl)-tetrahydrothiophene (compound No. 12-1)

To a stirred solution of trans-4-carboxy-2-(1-mercapto-1-methylethyl)tetrahydrothiophene (compound No. 8-1, 50 mg) in ethanol (3 ml), one drop of concentrated sulfuric acid was added under nitrogen atmosphere and the mixture was stirred for 1.5 hours. After cooling, the reaction mixture was week alkalized with aqueous sodium bicarbonate solution and extracted with ethyl acetate. The organic layer was washed with saturated sodium chloride solution, dried over anhydrous sodium sulfate and concentrated in vacuo to give 53 mg of the titled compound (compound No. 12-1).

IR (film, cm$^{-1}$): 2973, 2933, 2546, 1731, 1367, 1179.

Following compound can be prepared by the similar method as Example 12.

(2R,4R)-4-ethoxycarbonyl-2-mercaptomethyltetrahydrothiophene (compound No. 12-2)
$[\alpha]_D^{20}$ −113.1° (c=1.0, chloroform).
IR (film, cm$^{-1}$): 2978, 2935, 2559, 1731, 1445, 1371, 1181, 1032.

EXAMPLE 13 trans-2-(1-acetylthio-1-methylethyl)-4-carboxytetrahydrothiophene (compound No. 13-1)

trans-4-carboxy-2-(1-mercapto-1-methylethyl)tetrahydrothiophene (compound No. 8-1, 50 mg) was dissolved in a mixture of acetic anhydride (1 ml) and pyridine (1 ml) and the mixture was stirred over night at room temperature. The reaction mixture was concentrated in vacuo and the oily residue was purified by a silica gel column chromatography to give 43 mg (72%) of the titled compound (compound No. 13-1).

IR (film, cm$^{-1}$): 2968, 2936, 1709, 1688, 1109.

Following compounds can be prepared by the similar method as Example 13.

(2R,4R)-2-acetylthiomethyl-4-carboxytetrahydrothiophene (compound No. 13-2)
mp 76.6°-77.6° C. (n-hexane - ethyl acetate).
IR (KBr, cm$^{-1}$): 2936, 1688, 1455, 1420, 1354, 1286, 1137, 1106, 959, 628.

(2R,4R)-4-carboxy-2-pivaloylthiomethyltetrahydrothiophene (compound No. 13-3)

EXAMPLE 14

(2R,4R)-2-acetylthiomethyl-4-benzyloxycarbonyltetrahydrothiophene (compound No. 14-1)

To a stirred solution of (2R,4R)-2-acetylthiomethyl-4-carboxytetrahydrothiophene (compound No. 13-2, 0.18 g) in dimethylformamide (4 ml), benzyl bromide dissolved in dimethylformamide (4 ml) and diisopropylamine (214 μl) were added and the mixture was stirred over night. Water was added to the mixture and extracted with diethylether. The organic layer was washed with saturated sodium chloride solution, dried over anhydrous magnesium sulfate and concentrated in vacuo. The oily residue was purified by a silica gel column chromatography to give 0.18 g (71%) of the titled compound (compound No. 14-1).

IR (film, cm$^{-1}$): 2939, 1733, 1692, 1455, 1353, 1168, 1134, 957, 698, 626.

Following compounds can be prepared by the similar method as Example 14.

(2R,4R)-2-acetylthiomethyl-4-(4-methylbenzyloxycarbonyl)tetrahydrothiophene (compound No.14-2)

(2R,4R)-2-acetylthiomethyl-4-(4-methoxybenzyloxycarbonyl)tetrahydrothiophene (compound No.14-3)

(2R,4R)-2-acetylthiomethyl-4-(4-chlorobenzyloxycarbonyl)tetrahydrothiophene (compound No.14-4)

(2R,4R)-2-acetylthiomethyl-4-(4-ethoxycarbonylbenzyloxycarbonyl)tetrahydrothiophene (compound No.14-5)

EXAMPLE 15 trans-4-ethoxycarbonyl-2-mercaptomethyltetrahydrothiophene (compound No. 15-1)

To a stirred solution of cis-2,4-bis(mercaptomethyl)-4-butanolide (600 mg) in THF (20 ml), 1N sodium hydroxide solution (3.4 ml) was added and the mixture was stirred for 30 minutes at room temperature. The reaction mixture was acidified with 2N hydrochloric acid and extracted with ethyl acetate. The organic layer was washed with saturated sodium chloride solution, dried over anhydrous sodium sulfate and concentrated in vacuo to give crude trans-4-carboxy-2-mercaptomethyltetrahydrothiophene.

The crude product was dissolved in ethanol and one drop of concentrated sulfuric acid was added to the solution. The mixture was refluxed for 2.5 hours. After cooling the reaction mixture, the mixture was week alkalized with aqueous sodium bicarbonate solution and extracted with ethyl acetate. The organic layer was washed with water and saturated sodium chloride solution, dried over anhydrous magnesium sulfate and concentrated in vacuo. The oily residue was purified by a silica gel column chromatography to give 480 mg (69%) of the titled compound (compound No. 15-1).

IR (film, cm$^{-1}$): 2978, 2935, 2559, 1731, 1444, 1371, 1349, 1282, 1182, 1032, 862, 692.

Following compounds can be prepared by the similar method as Example 15.

cis-4-ethoxycarbonyl-2-mercaptomethyltetrahydrothiophene (compound No. 15-2) from trans-2,4-bis(mercaptomethyl)-4-butanolide IR (film, cm$^{-1}$): 2977, 2931, 2559, 1734, 1452, 1371, 1348, 1271, 1176, 1096, 1033, 859, 694.

trans-4-ethoxycarbonyl-2-mercaptomethyl-3-methyltetrahydrothiophene (compound No. 15-3) from cis-2,4-bis(mercaptomethyl)-3-methyl-4-butanolide IR (film, cm$^{-1}$): 2969, 2555, 1729, 1447, 1372, 1268, 1179, 1031, 860.

EXAMPLE 16 trans-4-carboxy-2-mercaptomethyl-tetrahydrothiophene (compound No. 7-1): Another synthetic method To a stirred solution of trans-4-ethoxycarbonyl-2-mercaptomethyltetrahydrothiophene (compound No. 15-1, 420 mg) in THF (28 ml), 1N lithium hydroxide solution (4.1 ml) was added and the mixture was stirred for 1.5 hours at room temperature. Water was added to the mixture and washed with ethyl acetate. The aqueous layer was acidified with dilute hydrochloric acid and extracted with ethyl acetate. The organic layer was washed with water and saturated sodium chloride solution, dried over anhydrous magnesium sulfate and concentrated in vacuo. The oily residue was purified by a silica gel column chromatography to give 254 mg (70%) of the titled compound (compound No. 7-1). The physical data was identified with the product obtained in Example 7.

Following compounds can be prepared by the similar method as Example 16.

cis-4-carboxy-2-mercaptomethyltetrahydrothiophene (compound No. 7-2)

The physical data was identified with the product obtained in Example 7.

trans-4-carboxy-2-mercaptomethyl-3-methyltetrahydrothiophene (compound No. 16-1)

mp 70.3°-71.4° C. (diisopropylether-n-hexane).

IR (KBr, cm$^{-1}$): 2965, 1692, 1418, 1284, 1225, 1198, 930, 746, 686, 527.

EXAMPLE 17 trans-4-carboxy-5-mercaptomethyltetrahydrothiophene (compound No. 17-1)

1) To a stirred solution of 5-ethoxycarbonyl-2,3-dihydrothiophene (500 mg) in dimethylformamide (3 ml), sodium cyanide (187 mg) was added under nitrogen atmosphere and the mixture was stirred for 2 days at room temperature. Water was added to the mixture and extracted with diethyl ether. The organic layer was washed with saturated sodium chloride solution, dried over magnesium sulfate and concentrated in vacuo. The oily residue was purified by a silica gel column chromatography to give 130 mg (24%) of trans-4-cyano-5-ethoxycarbonyltetrahydrothiophene.

IR (film, cm$^{-1}$): 2983, 2941, 2245, 1732, 1444, 1371, 1346, 1298, 1208, 1179, 1025.

2) Under nitrogen atmosphere, lithium bromide (208 mg) and sodium borohydride (50 mg) were dissolved in ethanol (3 ml) and the mixture was stirred for 45 minutes at room temperature. Under ice-cooling, trans-4-cyano-5-ethoxycarbonyltetrahydrothiophene (122 mg) dissolved in ethanol (2 ml) was added to the solution and the mixture was stirred over night. Aqueous ammonium chloride solution was added to the mixture under ice-cooling and extracted with ethyl acetate. The organic layer was washed with saturated sodium chloride solution, dried over anhydrous magnesium sulfate and concentrated in vacuo. The oily residue was purified by a silica gel column chromatography to give 90 mg (95%) of trans-4-cyano-5-hydroxymethyltetrahydrothiophene.

IR (film, cm$^{-1}$): 3419, 2940, 2871, 2243, 1442, 1384, 1264, 1131, 1057, 1024, 839.

3) To a stirred solution of trans-4-cyano-5-hydroxymethyltetrahydrothiophene (78 mg) and triphenylphosphine (283 mg) in THF (3 ml), diethylazodicarboxylate (188 mg) dissolved in THF (1.2 ml) and thioacetic acid (82 mg) dissolved in THF (1.2 ml) were added dropwise under ice-cooling and the mixture was stirred for 30 minutes. Saturated aqueous sodium bicarbonate solution was added to the mixture and extracted with diethylether. The organic layer was washed with saturated sodium chloride solution, dried over anhydrous magnesium sulfate and concentrated in vacuo. The oily residue was purified by a silica gel column chromatography to give 94 mg (86%) of trans-5-acetylthiomethyl-4-cyanotetrahydrothiophene.

IR (film, cm$^{-1}$): 2940, 2868, 2242, 1693, 1443, 1355, 1254, 1133, 956, 712, 625.

4) trans-5-acetylthiomethyl-4-cyanotetrahydrothiophene (65 mg) was dissolved in concentrated hydrochloric acid (1 ml) and the solution was refluxed for 10 minutes. After ice-cooling, sodium chloride solution was added to the mixture and extracted with ethyl acetate. The organic layer was washed with saturated sodium chloride solution, dried over anhydrous magnesium sulfate and concentrated in vacuo. The oily residue was purified by a silica gel column chromatography to give 12 mg (21%) of the titled compound (compound No. 17-1).

IR (film, cm$^{-1}$): 2934, 2554, 1698, 1417, 1300, 1126, 1063, 936, 853.

EXAMPLE 18 trans-4-ethoxycarbonyl-2-methylthiomethyltetrahydrothiophene (compound No. 18-1)

Diethylether solution of diazomethane (10 molar equivalents) was added to trans-4-ethoxycarbonyl-2-mercaptomethyltetrahydrothiophene (compound No. 15-1, 549 mg) and the mixture was stirred for 4 hours at room temperature. The mixture was concentrated in vacuo and the oil residue was purified by a silica gel column chromatography to give 407 mg (69%) of the titled compound (compound No. 18-1).

IR (film, cm$^{-1}$): 1731, 1371, 1281, 1186, 1031.

EXAMPLE 19 trans-4-carboxy-2-methylthiomethyltetrahydrothiophene (compound No. 19-1)

To a stirred solution of trans-4-ethoxycarbonyl-2-methylthiomethyltetrahydrothiophene (compound No. 18-1, 307 mg) in methanol (10 ml), 1N sodium hydroxide solution (2.8 ml) was added under nitrogen atmosphere and the mixture was stirred for 1 hour at room temperature. The mixture was acidified with 1N hydrochloric acid and concentrated in vacuo. Saturated aqueous sodium chloride solution was added to the aqueous residue and extracted with ethyl acetate. The organic layer was washed with water and saturated sodium chloride solution, dried over anhydrous sodium sulfate and concentrated in vacuo. The oily residue was purified by a silica gel column chromatography to give 260 mg (85%) of the titled compound (compound No. 19-1).

mp 74.8°-76.0° C. (n-hexane - ethyl acetate).

IR (KBr, cm$^{-1}$): 2956, 1698, 1427, 1273, 1252, 932.

EXAMPLE 20

(2R,4R)-4-(N,N-dimethylcarbamoyl)-2-mercaptomethyltetrahydrothiophene (compound No. 20-1)

To a stirred solution of N-succinimidyl (2R,4R)-2-mercaptomethyl-tetrahydrothiophene-4-carboxylate (compound No. 9-2, 204 mg) in dry THF (4 ml), 40% dimethylamine aqueous solution (0.14 ml) was added under ice-cooling and the mixture was stirred for 2 hours at room temperature. The mixture was acidified with 1N hydrochloric acid and extracted with ethyl acetate. The organic layer was washed with saturated sodium chloride solution, dried over anhydrous magnesium sulfate and concentrated in vacuo. The oily residue was purified by a silica gel column chromatography to give 17 mg (11%) of the titled compound (compound No. 20-1).

mp 41.8°-44.4° C.

$[\alpha]_D^{20}$ −93.8° (c=0.12, chloroform).

IR (KBr, cm$^{-1}$): 2927, 2528, 1621, 1493, 1416, 1252, 1120, 936, 700.

Following compounds can be prepared by the similar method as Example 20.

(2R,4R)-4-carbamoyl-2-mercaptomethyltetrahydrothiophene (compound No. 20-2)

mp 96.6°-98.1° C. (n-hexane - ethyl acetate).

$[\alpha]_D^{20}$ −103.2° (c=0.32, chloroform).

IR (KBr, cm$^{-1}$): 3374, 3210, 2946, 2927, 1640, 1418, 1269, 1129, 960, 737, 712, 657, 626.

(2R,4R)-N-[2-(4-imidazolyl)ethyl]-2-mercaptomethyl-4-tetrahydrothiophenecarboxamide (compound No. 20-3)

mp 129.1°-135.2° C.

$[\alpha]_D^{20}$ −71.7° (c=0.28, chloroform).

IR (KBr, cm$^{-1}$): 3186, 3017, 2928, 1652, 1567, 1449, 1086, 981, 818, 622.

(2R,4R)-N-(5-tert-butoxycarbonylaminopentyl)-2-mercaptomethyl-4-tetrahydrothiophenecarboxamide (compound No. 20-4)

mp 67.8°-71.0° C.

$[\alpha]_D^{20}$ −58.7° (c=0.1, chloroform)

IR (KBr, cm$^{-1}$): 3344, 2939, 2854, 1684, 1644, 1530, 1453, 1367, 1277, 1250, 1166, 670.

(2R,4R)-N-(5-carboxypentyl)-2-mercaptomethyl-4-tetrahydrothiophenecarboxamide (compound No. 20-5)

mp 65.6°-68.2° C.

$[\alpha]_D^{20}$ −70.5° (c=0.33, chloroform).

IR (KBr, cm$^{-1}$): 3301, 2930, 2863, 1705, 1638, 1543, 1437, 1411, 1293, 1265, 1211, 946, 657.

(2R,4R)-N-(5-hydroxypentyl)-2-mercaptomethyl-4-tetrahydrothiophenecarboxamide (compound No. 20-6)

mp 59.1°-60.6° C.

$[\alpha]_D^{20}$ −77.9° (c=0.29, chloroform).

IR (KBr, cm$^{-1}$): 3291, 2939, 2861, 1638, 1546, 1456, 1362, 1294, 1229, 1070, 662.

(2R,4R)-N-(5-methylaminopentyl)-2-mercaptomethyl-4-tetrahydrothiophenecarboxamide (compound No. 20-7)

(2R,4R)-N-(5-benzyloxycarbonylaminopentyl)-2-mercaptomethyl-4-tetrahydrothiophenecarboxamide (compound No. 20-8)

EXAMPLE 21

(2R,4R)-N-(5-aminopentyl)-2-mercaptomethyl-4-tetrahydrothiophenecarboxamide hydrochloride (compound No. 21-1)

(2R,4R)-N-(5-tert-butoxycarbonylaminopentyl)-2-mercaptomethyl-4-tetrahydrothiophenecarboxamide (compound No. 20-4, 35 mg) was added to 2.3N ethyl acetate solution of hydrogen chloride (3 ml) and the mixture was stirred for 2 hours at room temperature. The mixture was concentrated in vacuo and the oily residue was purified by a silica gel column chromatography to give 11.3 mg (39%) of the titled compound (compound No. 21-1).

$[\alpha]_D^{20}$ −32.6° (c=0.1, methanol).

IR (KBr, cm$^{-1}$): 3313, 2934, 2645, 2552, 2035, 1646, 1548, 1455, 1436, 1298, 1213, 675.

EXAMPLE 22 trans-4-carboxy-2-(1-phenylacetylthio-1-methylethyl)-tetrahydrothiophene (compound No. 22-1)

To a stirred solution of trans-4-carboxy-2-(1-mercapto-1-methylethyl)tetrahydrothiophene (compound No. 8-1, 87 mg) in pyridine (1.5 ml), phenylacetylchloride (85 mg) dissolved in methylene chloride (1 ml) was added under nitrogen atmosphere and the mixture was warmed at 90° C. Water and 1N hydrochloric acid were added to the reaction mixture and extracted with ethyl acetate. The organic layer was dried over anhydrous magnesium sulfate and concentrated in vacuo. The oily residue was purified by a silica gel column chromatography to give 6 mg (4.4%) of the titled compound (compound No. 22-1).

mp 67°-73° C.

IR (KBr, cm$^{-1}$): 3027, 2968, 2679, 1720, 1698, 1670, 1454, 1415, 1250, 1116, 1021, 716, 704.

EXAMPLE 23 trans-2-benzoylthiomethyl-4-ethoxycarbonyltetrahydrothiophene (compound No. 23-1)

To a stirred solution of trans-4-ethoxycarbonyl-2-mercaptomethyltetrahydrothiophene (compound No. 15-1, 60 mg) and triethylamine (42 μl) in methylene chloride (2 ml), benzoyl chloride (43 mg) dissolved in methylene chloride (1 ml) was added under ice-cooling. The mixture was stirred for 10 minutes and concentrated in vacuo. 0.1N hydrochloric acid was added to the residue and extracted with diethylether. The organic layer was washed with aqueous sodium bicarbonate solution and saturated sodium chloride solution, dried over anhydrous magnesium sulfate and concentrated in vacuo. The oily residue was purified by a silica gel column chromatography to give 77 mg (86%) of the titled compound (compound No. 23-1).

IR (film, cm$^{-1}$): 2979, 2936, 1731, 1666, 1448, 1371, 1207, 911, 689.

EXAMPLE 24

(+)-trans-4-carboxy-2-(1-mercapto-1-methylethyl)tetrahydrothiophene (compound No. 24-1) and (−)-trans-4-carboxy-2-(1-mercapto-1-methylethyl)tetrahydrothiophene (compound No. 24-2)

1) To a stirred solution of trans-4-carboxy-2-(1-mercapto-1-methylethyl)tetrahydrothiophene (compound No. 8-1, 2.9 g) in ethyl acetate (50 ml), R-(+)-naphthylethylamine (1.2 g) was added. Separated crystals was recrystallized with ethyl acetate. The crystals were added to 1N hydrochloric acid and extracted with ethyl acetate. The organic layer was washed with water and saturated sodium chloride solution, dried over anhydrous sodium sulfate and concentrated in vacuo. The oily residue was purified by a silica gel column chromatography to give 14 mg (0.5%) of (+)-compound (compound No. 24-1).

mp 75.9°–77.6° C.

$[\alpha]_D^{20}$ +83.7° (c=0.1, chloroform).

IR (KBr, cm$^{-1}$): 2968, 2547, 1701, 1453, 1415, 1365, 1258, 1200, 942.

2) To the first filtrate in the process 1), 1N hydrochloric acid was added. The organic layer was dried over anhydrous sodium sulfate and concentrated in vacuo. The oily residue was dissolved in ethyl acetate (30 ml) and S-(−)-naphthylethylamine (930 mg) was added to the solution. Separated crystals were recrystallized with ethyl acetate. The crystals were added to 1N hydrochloric acid and extracted with ethyl acetate. The organic layer was washed with water and saturated sodium chloride solution, dried over anhydrous sodium sulfate and concentrated in vacuo. The oily residue was purified by a silica gel column chromatography to give 16 mg (0.6%) of (−)-compound (compound No. 24-2).

mp 77.6°–79.0° C.

$[\alpha]_D^{20}$ −96.9° (c=0.1, chloroform).

IR (KBr, cm$^{-1}$): 2967, 2935, 2741, 2637, 2547, 1701, 1453, 1415, 1365, 1258.

EXAMPLE 25 trans-2-benzylthiomethyl-4-ethoxycarbonyltetrahydrothiophene (compound No. 25-1)

To a stirred solution of trans-4-ethoxycarbonyl-2-mercaptomethyltetrahydrothiophene (compound No. 15-1, 0.3 g) in ethanol (2 ml), sodium ethoxide (0.11 g) is added under nitrogen atmosphere and ice-cooling and the mixture is stirred for 30 minutes. Benzyl bromide (0.28 g) dissolved in ethanol (1 ml) was added to the mixture and the mixture is stirred for 30 minutes under ice-cooling and 1 hour at room temperature. Benzene is added to the reaction mixture. The organic layer is washed with water and saturated aqueous sodium chloride solution, dried over anhydrous sodium sulfate and concentrated in vacuo. The oily residue is purified by a silica gel column chromatography to give titled compound (compound No. 25-1).

Following compounds can be prepared by the similar method as Example 25.

trans-2-(4-ethoxycarbonylbenzylthiomethyl)-4-ethoxycarbonyltetrahydrothiophene (compound No. 25-2)

trans-2-tritylthiomethyl-4-ethoxycarbonyltetrahydrothiophene (compound No. 25-3)

PHARMACOLOGICAL TEST

Thymulin-like activities of the compounds of this invention were examined by modifying the method reported by J. F. Bach et al. (Bull. Inst. Pasteur, 76, 325 (1978)).

(Experimental Method)

A thymus of C57BL/6 strain male mouse (10 weeks age, 4 mice a group) was removed. After about two weeks, a spleen of the mouse was extracted and a spleen cells suspension (1×10$^8$ cells/ml in Hank's solution) was prepared. To 100 μl of the cells suspension, 100 μl of Hank's solution dissolving a test compound and zinc chloride in 1:1 molar ratio was added. After a 30 minutes incubation at 37° C., 50 μl of azathiopurine (50 μg/ml in Hank's solution) was added and the mixture was incubated further 60 minutes at the same temperature. To the mixture, 50 μl of sheep red blood cells (1×10$^8$ cells/ml in Hank's solution) was added and mixed. The mixture was incubated at 4° C. for one night. After gently shaking, E-rosette forming cells (E-RFC) were measured. As an active control, a solution of thymulin and zinc chloride, which were dissolved in Hank's solution in a concentration of 1×10$^{-14}$ M and 1:1 molar ratio, was used and it was treated by the same manner as the case of the test compound.

(Result)

Thymulin-like activity was calculated by the following formula.

$$\frac{\text{(E-RFC of a test compound)} - \text{(E-RFC of a control)}}{\text{(E-RFC of an active control)} - \text{(E-RFC of a control)}} \times 100 \, (\%)$$

Thymulin-like activities of the compounds of this invention having the basic structure represented by the formula [XVII] were measured. The compounds showed excellent activities. Especially, the compound No. 7-1, 8-1, 10-1, 10-2, 24-1 and 24-2 showed over than 50% of thymulin-like activity at a dose of lower than 10$^{-10}$M.

What we claim is:

1. A compound of the formula (I) and pharmaceutically acceptable salts thereof,

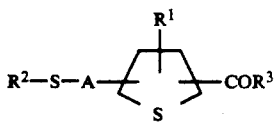 (I)

wherein
- $R^1$ is hydrogen or lower alkyl;
- $R^2$ is hydrogen, lower alkyl, lower alkenyl, lower alkanoyl, phenyl lower alkyl, phenylcarbonyl, phenyl lower alkylcarbonyl, trityl or tetrahydropyranyl, and the phenyl ring of the said phenyl lower alkyl, phenylcarbonyl or phenyl lower alkylcarbonyl is unsubstituted or substituted by lower alkyl, lower alkoxy, halogen, carboxy or lower alkoxycarbonyl;
- $R^3$ is hydroxy, lower alkoxy, lower alkenyloxy, phenyl lower alkoxy, N-succinimidoxy, amino or lower alkylamino, and the lower alkyl of the said lower alkylamino is unsubstituted or substituted by imidazolyl, carboxy, amino, lower alkylamino, lower alkoxycarbonylamino, phenyl lower alkoxycarbonylamino or hydroxy, and the phenyl ring of the said phenyl lower alkoxy or phenyl lower alkoxycarbonylamino is unsubstituted or substituted by lower alkyl, lower alkoxy, halogen, carboxy or lower alkoxycarbonyl, and
- A is straight or branched lower alkylene, and the sulfur atom in the side chain may be directly joined with —CO— to form a thiolactone ring.

2. The compound as in claim 1, wherein
$R^1$ is hydrogen or lower alkyl,
$R^2$ is hydrogen, lower alkyl, lower alkanoyl, phenyl lower alkyl, phenylcarbonyl or phenyl lower alkylcarbonyl;
$R^3$ is hydroxy, lower alkoxy, phenyl lower alkoxy, N-succinimidoxy, amino or lower alkylamino, and the lower alkyl of the said lower alkylamino can be substituted by imidazolyl, carboxy, amino, lower alkoxycarbonylamino or hydroxy, and
A is straight or branched lower alkylene.

3. The compound as in claim 1, wherein $R^1$ is hydrogen or lower alkyl; $R^2$ is hydrogen, and $R^3$ is hydroxy or lower alkoxy.

4. The compound as in claim 1, wherein each of $R^1$ and $R^2$ is hydrogen and $R^3$ is hydroxy.

5. The compound as in claim 1, wherein A is —CH$_2$— or

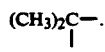

6. 4-carboxy-2-mercaptomethyltetrahydrothiophene.

7. 4-carboxy-2-(1-mercapto-1-methylethyl)tetrahydrothiophene.

8. (2R,4R)-4-carboxy-2-mercaptomethyltetrahydrothiophene.

9. A pharmaceutical composition comprising a compound of the formula (I) in accordance with claim 1, or salts thereof and pharmaceutically acceptable carrier therefor.

10. The compound as in claim 3, wherein A is —CH$_2$— or

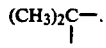

11. The compound as in claim 9, wherein A is —CH$_2$— or

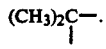

12. The compound as in claim 4, wherein A is —CH$_2$—.

13. The compound as in claim 4, wherein A is

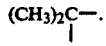

14. A compound of the formula (II) and pharmaceutically acceptable salts thereof,

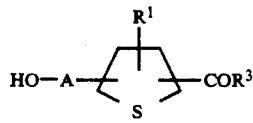 (II)

wherein
- $R^1$ is hydrogen or lower alkyl;
- $R^3$ is hydroxy, lower alkoxy, lower alkenyloxy, phenyl lower alkoxy, N-succinimidoxy, amino or lower alkylamino, and the lower alkyl of the said lower alkylamino is unsubstituted or substituted by imidazolyl, carboxy, amino, lower alkylamino, lower alkoxycarbonylamino, phenyl lower alkoxycarbonylamino or hydroxy, and the phenyl ring of the said phenyl lower alkoxy or phenyl lower alkoxycarbonylamino is unsubstituted or substituted by lower alkyl, lower alkoxy, halogen, carboxy or lower alkoxycarbonyl, and
- A is straight or branched lower alkylene.

15. The compound as in claim 1, wherein
$R^1$ is hydrogen, methyl, ethyl, propyl, hexyl, isopropyl or t-butyl,
$R^2$ is hydrogen, methyl, ethyl, propyl, hexyl, iso-propyl, tert-butyl, vinyl, allyl, hexenyl, acetyl, propionyl, hexanoyl, isopropionyl, pivaloyl, phenyl $C_1$–$C_6$ alkyl, phenylcarbonyl, phenyl $C_1$–$C_6$ alkylcarbonyl, trityl or tetrahydropyranyl, wherein the phenyl or said phenyl $C_1$–$C_6$ alkyl, phenylcarbonyl or phenyl $C_1$–$C_6$ alkylcarbonyl is unsubstituted or substituted by methyl, ethyl, propyl, hexyl, iso-propyl, tert-butyl, methoxy, ethoxy, propoxy, hexyloxy, iso-propoxy, tert-butoxy, fluorine, chlorine, bromine, iodine, carboxy or $C_1$–$C_6$ alkoxycarbonyl;
$R^3$ is hydroxy, methoxy, ethoxy, propoxy, hexyloxy, isopropoxy, tert-butoxy, $C_2$–$C_6$ alkenyloxy, phenyl $C_1$–$C_6$ alkoxy, N-succinimidoxy, amino or $C_1$–$C_6$ alkylamino, wherein the $C_1$–$C_6$ alkyl or said $C_1$–$C_6$ alkylamino is unsubstituted or substituted by imidazolyl, carboxy, amino, $C_1$–$C_6$ alkylamino, $C_1$–$C_6$ alkoxycarbonylamino, phenyl $C_1$–$C_6$ alkoxycarbonylamino or hydroxy, and the phenyl ring of said phenyl $C_1$–$C_6$ alkoxy or said phenyl $C_1$–$C_6$ alkoxycarbonylamino is unsubstituted or substituted by methyl, ethyl, propyl, hexyl, iso-propyl, tert-butyl, methoxy, ethoxy, propoxy, hexyloxy, iso-propyl, tert-butoxy, fluorine, chlorine, bromine, iodine, carboxy or $C_1$–$C_6$ alkoxycarbonyl.

* * * * *